US009249066B2

(12) United States Patent
Minoux et al.

(10) Patent No.: US 9,249,066 B2
(45) Date of Patent: Feb. 2, 2016

(54) DEHYDRATION OF ALCOHOLS ON ACIDIC CATALYSTS

(75) Inventors: Delphine Minoux, Nivelles (BE); Cindy Adam, Wierde (BE); Nikolai Nesterenko, Nivelles (BE); Sander Van Donk, Guildford (GB); Jean-Pierre Dath, Beloeil (BE); Walter Vermeiren, Houthalen (BE)

(73) Assignee: TOTAL RESEARCH & TECHNOLOGY FELUY, Seneffe (Feluy) (BE)

( * ) Notice: Subject to any disclaimer, the term of this patent is extended or adjusted under 35 U.S.C. 154(b) by 0 days.

(21) Appl. No.: 13/701,774

(22) PCT Filed: Jun. 20, 2011

(86) PCT No.: PCT/EP2011/060212
§ 371 (c)(1),
(2), (4) Date: Feb. 15, 2013

(87) PCT Pub. No.: WO2011/161045
PCT Pub. Date: Dec. 29, 2011

(65) Prior Publication Data

US 2013/0217943 A1 Aug. 22, 2013

(30) Foreign Application Priority Data

Jun. 23, 2010 (EP) .................................... 10166980
Aug. 3, 2010 (EP) .................................... 10171676

(51) Int. Cl.
*C07C 1/24* (2006.01)

(52) U.S. Cl.
CPC ............... *C07C 1/24* (2013.01); *C07C 2521/04* (2013.01); *C07C 2521/06* (2013.01); *C07C 2521/12* (2013.01); *C07C 2529/40* (2013.01); *C07C 2529/65* (2013.01); *C07C 2529/82* (2013.01); *C07C 2529/83* (2013.01); *C07C 2529/85* (2013.01)

(58) Field of Classification Search
CPC .................................. C07C 1/24; C07C 11/04
USPC .................................................. 585/638–640
See application file for complete search history.

(56) References Cited

U.S. PATENT DOCUMENTS

| | | | | |
|---|---|---|---|---|
| 2,220,430 | A | 11/1940 | Stanley | |
| 3,911,041 | A | 10/1975 | Kaeding et al. | |
| 4,234,752 | A | 11/1980 | Wu et al. | |
| 4,302,357 | A | 11/1981 | Kojima et al. | |
| 4,517,395 | A | 5/1985 | Obenaus et al. | |
| 4,873,392 | A | 10/1989 | Le Van Mao | |
| 5,573,990 | A | 11/1996 | Wang et al. | |
| 5,714,662 | A * | 2/1998 | Vora et al. | 585/640 |
| 8,426,664 | B2 * | 4/2013 | Bailey et al. | 585/639 |
| 8,710,288 | B2 * | 4/2014 | Liu et al. | 585/639 |
| 2003/0065233 | A1 | 4/2003 | Fuji et al. | |
| 2003/0078463 | A1 * | 4/2003 | Martens et al. | 585/638 |
| 2004/0045873 | A1 | 3/2004 | Olivier et al. | |
| 2007/0027351 | A1 * | 2/2007 | Dath et al. | 585/639 |

FOREIGN PATENT DOCUMENTS

| | | | |
|---|---|---|---|
| GB | 1009943 | A | 11/1965 |
| WO | 2009092779 | A2 | 7/2009 |
| WO | 2009092781 | A2 | 7/2009 |
| WO | 2009098262 | A1 | 8/2009 |

OTHER PUBLICATIONS

Ramesh, K., et al., "Synthesis, Characterization, and Catalytic Activity of Phosphorus Modified H-ZSM-5 Catalysts in Selective Ethanol Dehydration", Industrial & Engineering Chemistry Research, vol. 49, No. 9, pp. 4080-4090.
Office Action issued in Chinese Application No. 201180040471.X dated Apr. 24, 2014, and an English translation thereof (17 pages).
K. Jiratova, L. Beranek, "Properties of Modified Aluminas", Appl. Catal. 2 (1982) 125-138.
R. Miranda. D.J. Colins, "Catalytic Conversion of Alcohols: Role of Sodium in Altering the Alkene Products Obtained with Alumina Catalysts", J. Catal. 88 (1984) 542-454.
Office Action issued in European Application No. 11726774.0, dated Oct. 9, 2015, 7 pages.

* cited by examiner

*Primary Examiner* — In Suk Bullock
*Assistant Examiner* — Sharon Pregler

(57) ABSTRACT

A dehydration process may include introducing in a reactor an alcohol, and contacting the alcohol with an acidic catalyst to dehydrate the alcohol to make a corresponding olefin. The process may include recovering from the reactor the olefin and water. In the process, an effective amount of a component capable to neutralize a part of the catalyst active site may be introduced. The component may include ammonia, organic ammonium salts, hydrazine, nitriles, amines, amides, imines, di-imines, imides, cyanates, isocyanates, nitrites and nitroso compounds, aldehydes, ketones, carboxylic esters, and their corresponding thio-compounds.

25 Claims, 3 Drawing Sheets

Figure 1- Evolution of the ethanol conversion (filled symbols) and the ethylene yield (open symbols) as a function of time of stream. Surfin 96 bio-ethanol – 400°C -2bara – WHSV(Ethanol): $7h^{-1}$ Figure 2- Evolution of the ethanol conversion (filled symbols) and the ethylene yield (open symbols) as a function of time of stream : bio-ethanol spiked with 0.8ppmwt acetonitrile 430°C ; 2bara ; WHSV(EtOH): $7h^{-1}$ Figure 3 - Evolution of the ethanol conversion (filled symbols) and the ethylene yield (open symbols) as a function of time of stream at 430°C / Surfin96 bio-ethanol ; 2bara ; WHSV(EtOH): 7h-1

DEHYDRATION OF ALCOHOLS ON ACIDIC CATALYSTS

CROSS-REFERENCE TO RELATED APPLICATIONS

This application claims the benefit of PCT/EP2011/060212, filed Jun. 20, 2011, which claims priority from EP 10166980.2, filed Jun. 23, 2010 and EP 10171676.9 filed Aug. 3, 2010.

FIELD OF THE INVENTION

The present invention relates to the dehydration of alcohols on acidic catalysts to make olefins, more precisely the corresponding olefin which means an olefin having the same number of carbons as the alcohol precursor. The limited supply and increasing cost of crude oil has prompted the search for alternative processes for producing hydrocarbon products such fuels and such as ethylene, propylene and butenes. Ethanol can be obtained by fermentation of carbohydrates. Made up of organic matter from living organisms, biomass is the world's leading renewable energy source. The dehydration is made in the presence of an acidic catalyst such as alumina's, silicated, zirconated, titanated or fluorated alumina's, silica-alumina's and zeolite based catalyst.

In the alcohol dehydration process, alcohol conversion is nearly complete. However, it is of particular importance to limit the amounts of secondary products to gain in process efficiency and to save expensive steps of downstream separation/purification: in the case of ethanol dehydration, significant benefits could be done by increasing $C_2^-$ (ethylene) selectivity while maintaining optimal $C_2^-$ yields. The same accounts for propanol and butanol dehydration into their corresponding olefins, namely propylene and butenes. It is well understood by the persons in the art that commercial acidic catalysts exhibit acid sites with a distribution of acidic strengths and a variations in local acid site density. For a given catalytic reaction, like dehydration of one single alcohol, only a certain acid strength and density will result in optimal conversion and selectivity for the desired product. Non-optimal acid sites will result in different reactions and result in undesirable reaction products. Furthermore, the occurrence of unselective reaction depends also on the residence time of the feed in the catalytic reactor, on the reaction temperature and on the presence of trace components present in the feed that can temper the activity of certain acid sites. The combined effect of these parameters (acid site distribution, local acid site density, reaction temperature, residence time and feed composition) will determine the catalytic selectivity.

The unselective reactions that need to be suppressed are (i) altering in number of carbon atoms compared to the alcohol through oligomerisation and cracking reactions and (ii) the formation of paraffins and aromatics or coke through hydrogen-transfer reactions.

A convenient solution has been discovered to adjust the activity and selectivity of an alcohol dehydration catalyst by poisoning the unselective acid sites by spiking the feed with a neutralizing agent while keeping active the selective acidic sites.

The present invention relates in one embodiment to a method for the dehydration of substantially one single alcohol characterised by an increased selectivity for the corresponding olefin with the same number of carbon atoms by tempering the unselective catalytic acid sites using appropriate spiking of the alcohol feed with a neutralising agent.

In another embodiment the amount of neutralising agent can be adjusted during the use of the catalyst to compensate for changes in feed residence time, the feed composition and loss of catalyst activity through deactivation.

In still another embodiment the reaction temperature can be increased to maximise conversion while adding neutralising agent to the feed or while already neutralising components are present in the feed.

BACKGROUND OF THE INVENTION

U.S. Pat. No. 4,302,357 relates to an activated alumina catalyst employed in a process for the production of ethylene from ethanol through a dehydration reaction. In the description LHSV of ethanol is from 0.25 to 5 $h^{-1}$ and preferably from 0.5 to 3 $h^{-1}$. The examples are carried out at 370° C. and LHSV of 1 $h^{-1}$, ethylene yield is from 65 to 94%.

Process Economics Reviews PEP' 79-3 (SRI international) of December 1979 describes the dehydration of an ethanol-water (95/5 weight %) mixture on a silica-alumina catalyst in a tubular fixed bed at 315-360° C., 1.7 bar absolute and a WHSV (on ethanol) of 0.3 $h^{-1}$. The ethanol conversion is 99% and the ethylene selectivity is 94.95%. It also describes the dehydration of an ethanol-water (95/5 weight %) mixture on a silica-alumina catalyst in a fluidized bed at 399° C., 1.7 bar absolute and a WHSV (on ethanol) of 0.7 $h^{-1}$. The ethanol conversion is 99.6% and the ethylene selectivity is 99.3%.

U.S. Pat. No. 4,873,392 describes a process for converting diluted ethanol to ethylene which comprises heating an ethanol-containing fermentation broth thereby to vaporize a mixture of ethanol and water and contacting said vaporized mixture with a ZSM-5 zeolite catalyst selected from the group consisting of:

- a ZSM-5 zeolite having a Si/Al atomic ratio of from 5 to 75 which has been treated with steam at a temperature ranging from 400 to 800° C. for a period of from 1 to 48 hours;
- a ZSM-5 zeolite having a Si/Al atomic ratio of from 5 to 50 and wherein La or Ce ions have been incorporated in a weight percentage of 0.1 to 1.0% by ion exchange or in a weight percentage ranging from 0.1 to 5% by impregnation, and
- a ZSM-5 zeolite having a Si/Al of from 5 to 50 and impregnated with a 0.5 to 7 wt % of trifluoromethanesulfonic acid, and recovering the ethylene thus produced.

In ex 1 the catalyst is a steamed ZSM-5 having a Si/Al ratio of 21, the aqueous feed contains 10 w % of ethanol and 2 w % of glucose, the temperature is 275° C., the WHSV is from 3.2 to 38.5 $h^{-1}$. The ethylene yield decreases with the increase of WHSV. The ethylene yield is 99.4% when WHSV is 3.2 $h^{-1}$ and 20.1% when WHSV is 38.5 $h^{-1}$.

In ex 2 a ZSM-5 having a Si/Al ratio of 10 is compared with the same but on which La or Ce ions have been incorporated. The aqueous feed contains 10 w % of ethanol and 2 w % of glucose, the temperature is from 200° C. to 225° C., the WHSV is 1 $h^{-1}$ and the best ethylene yield is 94.9%.

In ex 3 the catalyst is a ZSM-5 having a Si/Al ratio of 10 on which trifluoromethanesulfonic acid has been incorporated, the aqueous feed contains 10 w % of ethanol and 2 w % of glucose, the temperature is from 180° C. to 205° C., the WHSV is 1 $h^{-1}$. The ethylene yield increases with temperature (73.3% at 180° C., 97.2% at 200° C.) and then decreases (95.8% at 205° C.).

In the ethanol dehydration processes, ethanol conversion is nearly complete. The increase of C2− selectivity while keeping high ethanol conversion is of importance to gain in process efficiency and to save expensive steps of downstream separation/purification. A convenient solution has been discovered to adjust the activity and selectivity of the catalyst by poisoning the unselective acid sites while keeping active the selective acidic sites. This can be achieved by an appropriate spiking of the alcohol feed with a neutralising agent. A particular characteristic of the present invention is that the amount of neutralising agent to maximise selectivity can be adjusted continuously and eventually completely omitted from the reaction section. Such event can occur when (i) the residence time of the feed in the catalytic reactor changes, (ii) when the feed composition changes and contains similar neutralising components or (iii) when the catalyst deactivates due to poising or coke lay down on the catalyst surface.

The moderation of the catalytic activity by feed spiking the feedstock is documented for other processes but not for alcohol dehydration.

For instance, U.S. Pat. No. 4,517,395 discloses the addition of fixed amounts of carbon monoxide (CO), which increases the selectivity of the hydrogenation process towards the conversion of conjugated and/or cumulative double bonds and for acetylenic triple bonds into monoene-containing mixtures of hydrocarbons, so as to avoid to a maximum extend any losses of monoenes by the formation of saturated hydrocarbons.

Another example is to find in U.S. Pat. No. 7,399,402 which describes the introduction of an ammonia precursor when hydrotreating a C4-C8 hydrocarbon feed rich in olefins and aromatics on a catalyst consisting of transition metals supported on refractory oxides. The introduction of the ammonia precursor into the feed allows to block the acid sites responsible for secondary reactions (oligomerization and alkylation on acid sites in this prior art), thus keeping excellent product quality.

In order to avoid the double bond isomerisation of the primary alpha-olefins in the dehydration of long-chain alcohols, the use of metal cations to modify the catalyst (by minimizing the number of acid sites that are thought to increase the rate of isomerization) have been reported (K. Jira'tova', L. Bera'nek, Appl. Catal. 2 (1982) 125; R. Miranda, D. J. Collins, J. Catal. 88 (1984) 542 and U.S. Pat. No. 4,234,752). Such methods are permanent, irreversible and hence no means are left available to adjust the performance when feed composition, feed residence time and catalyst activity changes over the time of using the catalyst.

U.S. Pat. No. 4,873,392 mentions at col 1 line 48-col 2 line 9 a modification of the ZSM-5 acid sites if the production of ethylene is desired. This part of U.S. Pat. No. 4,873,392 relates to the MTO reaction in which methanol is converted to a mixture of ethylene, propylene and higher hydrocarbons. It has nothing to see with the present invention which relates to the dehydration of alcohols on acidic catalysts to make the corresponding olefin which means an olefin having the same number of carbons as the alcohol precursor.

BRIEF SUMMARY OF THE INVENTION

The present invention is, in an embodiment 1, a process for the dehydration of an alcohol having at least 2 carbon atoms to make the corresponding olefin, comprising:

a) introducing in a reactor a stream (A) comprising at least an alcohol, optionally water, optionally an inert component, b) contacting said stream with an acidic catalyst in said reactor at conditions effective to dehydrate at least a portion of the alcohol to make an olefin, c) recovering from said reactor a stream (B) comprising: the inert component and at least an olefin, water and optionally unconverted alcohol, d) optionally fractionating the stream (B) to recover the unconverted alcohol and recycling said unconverted alcohol to the reactor of step a), e) optionally fractionating the stream (B) to recover the inert component, water and the olefin and optionally recycling said inert component and optionally a part of the water to the reactor of step a), wherein, f) an effective amount of a component capable to neutralize a part of the catalyst active site is introduced in stream (A) or directly in the dehydration reactor and g) optionally the temperature of the dehydration reactor is adjusted to increase the alcohol conversion or the olefin yield or both.

As a result of said addition at step f) the selectivity for the desired corresponding olefin is increased.

The present invention is, in an embodiment 2, a process for the dehydration of an alcohol having at least 2 carbon atoms to make the corresponding olefin, comprising:

a) introducing in a reactor a stream (A) comprising at least an alcohol, optionally water, optionally an inert component, b) contacting said stream with an acidic catalyst in said reactor at conditions effective to dehydrate at least a portion of the alcohol to make an olefin, c) recovering from said reactor a stream (B) comprising: the inert component and at least an olefin, water and optionally unconverted alcohol, d) optionally fractionating the stream (B) to recover the unconverted alcohol and recycling said unconverted alcohol to the reactor of step a), e) optionally fractionating the stream (B) to recover the inert component, water and the olefin and optionally recycling said inert component and optionally a part of the water to the reactor of step a), wherein, f) an effective amount of a component capable to increase the selectivity for the desired corresponding olefin is introduced in stream (A) or directly in the dehydration reactor and g) optionally the temperature of the dehydration reactor is adjusted to increase the alcohol conversion or the olefin yield or both.

In an embodiment the catalyst is:

A crystalline silicate zeolite having a ratio Si/Al higher than 10,

A dealuminated crystalline silicate zeolite,

A phosphorous modified zeolite, silica-alumina, alumina, silicated, titanated, zirconated or fluorinated alumina or silico-aluminophosphates In an embodiment the temperature ranging from 280 to 500° C. is adjusted so as the resistance against poisoning of the catalyst is achieved by reducing the adsorption equilibrium on the catalyst surface by the neutralising components, thus allowing to achieve optimal catalyst stability independently from the nature and content of the impurities contained in the alcohol derived from biomass. The spiking component (the component injected at step f)) is essentially a nitrogen-containing compound that is basic in nature or can be transformed into a basic component under the reaction conditions of dehydration and can be selected from the group consisting of ammonia, organic ammonium salts, hydrazine, nitriles, amines (including pyridines, pyrrols, pyrrolydones and pyrrolidines), amides, imines, di-imines, imides, cyanates, isocyanates, nitrites and nitroso compounds, aldehydes, ketones, carboxylic esters, and their corresponding thio-compounds (thiols, sulphides, disulfides).

Without willing to be bound to any theory, it is believed that a dynamic equilibrium is installed between the added neutralising agent or its derived components, produced under the dehydration reaction conditions, that is present in the feed and the catalyst surface. The amount of neutralising agent or its derived components, produced under the dehydration reaction conditions that is adsorbed on the unselective acid sites is determined by its partial pressure above the catalyst surface and by the temperature. Hence the requirement to improve the selectivity of the catalyst can be fulfilled by the amount of added or present neutralising agent in the feed and by the reaction temperature. It is understood that the effective component that is able to neutralise unselective acid sites has to be basic in nature. Some of the above mentioned nitrogen-containing compounds are basic whereas others easily decompose into basic nitrogen compounds under the reaction conditions (high temperature and presence of water).

DETAILED DESCRIPTION OF THE INVENTION

Figure 1:
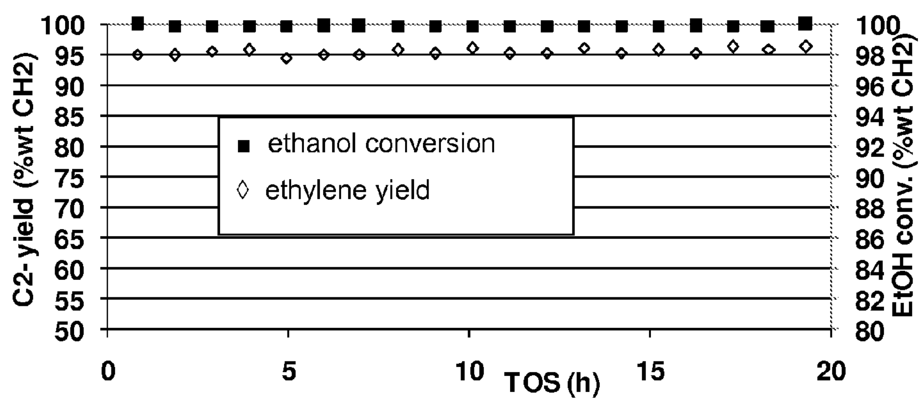
FIG. 1 shows the evolution of ethanol conversion and ethylene yield as a function of time on stream.

As regards the stream introduced at step a) the alcohol is any alcohol provided it can be dehydrated to the corresponding olefin. By way of example mention may be made of alcohols having from 2 to 10 carbon atoms. Advantageously the invention is of interest for ethanol, propanol, butanol (iso, n and tertio) and phenylethanol.

The inert component is any component provided there is no adverse effect on the catalyst. Because the dehydration is endothermic the inert component can be used to bring energy. By way of examples the inert component is selected among the saturated hydrocarbons having up to 10 carbon atoms, naphtenes, nitrogen and CO2. An example of inert component can be any individual saturated compound, a synthetic mixture of the individual saturated compounds as well as some equilibrated refinery streams like straight naphtha, butanes etc. Advantageously it is a saturated hydrocarbon or a mixture of saturated hydrocarbons having from 3 to 7 carbon atoms, more advantageously having from 4 to 6 carbon atoms and is preferably pentane. The weight proportions of respectively alcohols, water and inert component are, for example, 5-100/0-95/0-95 (the total being 100). The stream (A) can be liquid or gaseous.

As regards the dehydration reactor, it can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The dehydration may be performed continuously in a fixed bed reactor configuration using a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

As regards the pressure in steps a) and b), the pressure of the reactor of step b) can be any pressure but it is more economical to operate at moderate pressure. By way of example the pressure of the reactor ranges from 0.5 to 30 bars absolute (50 kPa to 3 MPa), advantageously from 0.5 to 10 bars absolute (50 kPa to 1 MPa), advantageously from 0.5 to 5 bars absolute (50 kPa to 0.5 MPa), more advantageously from 1.2 to 5 bars absolute (0.12 MPa to 0.5 MPa) and preferably from 1.2 to 4 bars absolute (0.12 MPa to 0.4 MPa). Advantageously, the partial pressure of the alcohols is advantageously lower than 4 bars absolute (0.4 MPa) and more advantageously from 0.5 to 4 bars absolute (0.05 MPa to 0.4 MPa), preferably lower than 3.5 bars absolute (0.35 MPa) and more preferably lower than 2 bars absolute (0.2 MPa).

As regards the temperature of the dehydration reactor, it ranges advantageously from 280° C. to 500° C., more advantageously from 300° C. to 500° C. and preferably from 330° C. to 450° C.

These reaction temperatures refer substantially to average catalyst bed temperature. The ethanol dehydration is an endothermic reaction and requires the input of reaction heat in order to maintain catalyst activity sufficiently high and shift the thermodynamic equilibrium to sufficiently high conversion levels.

In case of fluidised bed reactors: (i) for stationary fluidised beds without catalyst circulation, the reaction temperature is substantially homogeneous throughout the catalyst bed; (ii) in case of circulating fluidised beds where catalyst circulates between a converting reaction section and a catalyst regeneration section, depending on the degree of catalyst backmixing the temperature in the catalyst bed approaches homogeneous conditions (a lot of backmixing) or approaches plug flow conditions (nearly no backmixing) and hence a decreasing temperature profile will install as the conversion proceeds.

In case of fixed bed or moving bed reactors, a decreasing temperature profile will install as the conversion of the alcohol proceeds. In order to compensate for temperature drop and consequently decreasing catalyst activity or approach to thermodynamic equilibrium, reaction heat can be introduced by using several catalyst beds in series with interheating of the reactor effluent from the first bed to higher temperatures and introducing the heated effluent in a second catalyst bed, etc. When fixed bed reactors are used, a multi-tubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

As regards the WHSV of the alcohol, it ranges advantageously from 1 to 20 $h^{-1}$, more advantageously from 2 to 20 $h^{-1}$, preferably from 5 to 15 $h^{-1}$, more preferably from 7 to 12 $h^{-1}$.

As regards the stream (B), it comprises essentially water, olefin, the inert component (if any) and unconverted alcohol. Said unconverted alcohol is supposed to be as less as possible. The olefin is recovered by usual fractionation means. Advantageously the inert component, if any, is recycled in the stream (A) as well as the unconverted alcohol, if any.

As regards the dehydration catalyst of step b), it can be any acid catalyst capable to cause the dehydration of alcohols under above said conditions. One can cite molecular sieves, zeolites, modified zeolites (including P-modified zeolites)

silica-alumina, alumina, silicated, titanated, zirconated or fluorinated alumina, silico-aluminophosphates.

According to an embodiment the catalyst is a crystalline silicate containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron. Advantageously in said first embodiment the catalyst (A1) is a crystalline silicate or a dealuminated crystalline silicate.

The crystalline silicate can have a ratio Si/Al of at least about 10.

The crystalline silicate, in an embodiment, can have a ratio Si/Al of at least about 100 and is advantageously selected among the MFI and the MEL.

The crystalline silicate and the dealuminated crystalline silicate are essentially in H-form. It means that a minor part (less than about 50%) can carry metallic compensating ions e.g. Na, Mg, Ca, La, Ni, Ce, Zn, Co.

The dealuminated crystalline silicate is advantageously such as about 10% by weight of the aluminium is removed. Such dealumination is advantageously made by a steaming optionally followed by a leaching. Such dealumination is advantageously made by a steaming optionally followed by a leaching.

In another specific embodiment the crystalline silicate catalyst is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicate, metal oxides (such as $Zr0_2$) or gels including mixtures of silica and metal oxides.

According to an embodiment the catalyst is a P-modified zeolite (Phosphorus-modified zeolite). Said phosphorus modified molecular sieves can be prepared based on MFI, MOR, MEL, clinoptilolite or FER, MWW, TON, EUO, MFS and ZSM-48 family of microporous molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:

- selecting a zeolite (advantageously with Si/Al ratio between 4 and 500) among $H^+$ or $NH_4^+$-form of MFI, MEL, FER, MOR, clinoptilolite, MWW, TON, EUO, MFS and ZSM-48;
- introducing P at conditions effective to introduce advantageously at least 0.05 wt % of P;
- separation of the solid from the liquid if any;
- an optional washing step or an optional drying step or an optional drying step followed by a washing step;
- a calcination step;

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. No. 3,911,041, U.S. Pat. No. 5,573,990 and U.S. Pat. No. 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product. Advantageously, at least a part of phosphorous is introduced into zeolite before shaping. In a specific embodiment, the formed P-precursor can be further modified with the metals selected from Mg, Ca, La, Ni, Ce, Zn, Co, Ag, Fe, Cu according to the recipe described in WO 09092779 and WO 09092781.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final equilibration step is performed advantageously at the temperature 400-800° C. either in a static condition or in a gas flow. Air, nitrogen or any inert gases can be used.

According to a specific embodiment the phosphorous modified zeolite is made by a process comprising in that order:

- selecting a zeolite (advantageously with Si/Al ratio between 4 and 500, from 4 to 30 in a specific embodiment) among $H^+$ or $NH_4^+$-form of MFI, MEL, FER, MOR, clinoptilolite, MWW, TON, EUO, MFS and ZSM-48;
- steaming at a temperature ranging from 400 to 870° C. for 0.01-200 h;
- leaching with an aqueous acid solution at conditions effective to remove a substantial part of Al from the zeolite;
- introducing P with an aqueous solution containing the source of P at conditions effective to introduce advantageously at least 0.05 wt % of P;
- separation of the solid from the liquid;
- an optional washing step or an optional drying step or an optional drying step followed by a washing step;
- a calcination step.

Optionally between the steaming step and the leaching step there is an intermediate step such as, by way of example, contact with silica powder and drying.

Optionally the leaching and introducing P are made simultaneously by using an acid based comprising phosphorus to make the leaching.

Advantageously the selected MFI, MEL, FER, MOR, clinoptilolite, MWW, TON, EUO, MFS and ZSM-48 (or $H^+$ or $NH_4^+$-form MFI, MEL, FER, MOR, clinoptilolite, MWW, TON, EUO, MFS and ZSM-48) has an initial atomic ratio Si/Al of 100 or lower and from 4 to 30 in a specific embodiment. The conversion to the $H^+$ or $NH_4^+$-form is known per se and is described in U.S. Pat. No. 3,911,041 and U.S. Pat. No. 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, MWW, TON, EUO, MFS and ZSM-48, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said P-modified zeolite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of P-modified zeolite which is contained in the final catalyst product ranges from 10 to 90 weight percent of the total catalyst, preferably 20 to 70 weight percent of the total catalyst.

A dehydration catalyst has already been described in WO2009098262.

According to another specific embodiment, suitable catalysts for the present process is the silicoaluminophosphate molecular sieves, in particular of the AEL group with typical example the SAPO-11 molecular sieve. The SAPO-11 molecular sieve is based on the ALPO-11, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (Al+P+Si is 100).

Another family of suitable catalysts for the dehydration are alumina's as such, silica-alumina's or alumina's that have been modified by surface treatment with silicon, zirconium, titanium or fluor. Alumina's are generally characterised by a rather broad acid strength distribution and having both Lewis-type and Bronsted-type acid sites. The presence of a broad acid strength distribution makes the catalysis of several reactions, requiring each a different acid strength, possible. This often results in low selectivity for the desired product. Deposition of silicon, zirconium, titanium or fluor on the surface of alumina allows rendering the catalyst significantly more selective. For the preparation of the alumina based catalyst, suitable commercial alumina's can be used, preferably eta or gamma alumina, having a surface area of 10 to 500 m2/gram and an alkali content of less than 0.5%. The catalyst according to the present invention is prepared by adding 0.05 to 10% of silicon, zirconium or titanium. The addition of these metals can be done during the preparation of the alumina or can be added to the existing alumina, eventually already activated. Addition of the metal during the preparation of the alumina can be done by dissolving the metal precursor together with the aluminium precursor before precipitation of the final alumina or by addition of the metal precursor to the aluminium hydroxide gel. A preferred method is adding metal precursors to the shaped alumina. Metal precursors are dissolved in a suitable solvent, either aqueous or organic, and contacted with the alumina by incipient wetness impregnation or by wet impregnation or by contacting with an excess of solute during a given time, followed by removing the excess solute. The alumina can also be contacted with vapour of the metal precursor. Suitable metal precursors are halides of silicon, zirconium or titanium, oxyhalides of zirconium or titanium; alcoxides of silicon, zirconium or titanium; oxalates or citrates of zirconium or titanium or mixtures of the above. The solvent is selected according to the solubility of the metal precursor. The contacting can be done at temperature of 0° C. to 500° C., most preferred from 10° C. to 200° C. After the contacting, the alumina is eventually washed, dried and finally calcined in other to enhance the surface reaction between the silicon, zirconium or titanium and the alumina and the removal of the metal precursor ligands. The use of silicated, zirconated or titanated or fluorinated alumina's for the dehydration is preferably done in the presence of water. The weight ratio of water to alcohol ranges from 1/25 to 3/1. Fluorinated alumina is known in itself and can be made according to the prior art.

As regards the component of step f), it can be selected among the compounds able to neutralize (directly as of its basic nature or indirectly by its decomposition products under the operating conditions) a part of the catalyst unselective active sites. More specifically, it can be chosen from the group consisting of ammonia, organic ammonium salts, hydrazine, nitriles, amines (including pyridines, pyrrols, pyrrolydones and pyrrolidines), amides, imines, di-imines, imides, cyanates, isocyanates, nitrites and nitroso compounds.

In another embodiment, it can be chosen from the group consisting of aldehydes, ketones, carboxylic esters In another embodiment, it can be chosen from the group consisting of thiols, sulphides, disulfides.

The amount is advantageously in the range 0.001 ppm to 100 wppm relative to the alcohol, advantageously from 0.01 wppm to 100 wppm, and more preferably from 0.01 to 10 ppmwt. The neutralising agent can be introduced in the reactor by (i) blending with the alcohol feedstock, (ii) blending with a part of the alcohol feedstock which is subsequently introduced in the reactor with the remaining alcohol feedstock, (iii) blended with the inert diluents which is subsequently introduced in the reactor with the alcohol feedstock, (iv) blended with water which is subsequently introduced in the reactor with the alcohol feedstock, (v) blended with one the streams that is recycled back to the reactor, like non-converted alcohol, water or inert diluents or (vi) blending an alcohol feedstock being substantially free from neutralising agents with an alcohol feedstock containing already in the range of 0.001 wppm to 1000 wppm neutralising agent. In the latter case the neutralising agent is originating from the production process where the alcohol feedstock was produced as for instance the fermentation process of carbohydrates or synthesis gas into alcohol where trace amounts of neutralising agent are inherently part of the production process and are left in the final alcohol product. In an extreme case, only alcohol feedstock containing already neutralising agents in appropriate quantities is used. In the latter case, adjusting the reaction temperature allows to control the effect of the neutralising agent for its ability to temper the impact of unselective acid sites. In another embodiment, as the active component of the neutralising agent or the neutralising agent itself is, directly or indirectly, in dynamic equilibrium with the catalyst, a part or substantially all of it will leave the reactor together with the olefin, water and inert diluents and a part or substantially all can be concentrated in one of the streams that are recycled back to the reactor. Depending on the nature of the active component leaving the reactor, it may concentrate in the non-converted alcohol, the inert diluent or the aqueous fraction, containing eventually also non-converted alcohol and inert diluents. In such case the active component or the neutralising agent is recycled back to the reactor where it contributes to the dynamic equilibrium with the catalyst. Doing so, the make-up of neutralising agent can be lowered significantly.

As regards the temperature of the dehydration reactor to be adjusted, it is easily made by the operator in charge of the reactor by checking the conversion and yield. Advantageously said adjustment is an increase of about 5 to 50° C., preferably of about 10 to 40° C., more preferably 20 to 40° C.

EXAMPLES

The ethanol conversion is the ratio (ethanol introduced in the reactor−ethanol leaving the reactor)/(ethanol introduced in the reactor).

The ethylene yield is the ratio, on carbon basis, (ethylene leaving the reactor)/(ethanol introduced in the reactor).

The ethylene selectivity is the ratio, on carbon basis, (ethylene leaving the reactor)/(ethanol converted in the reactor).

The ethylene purity is the ratio, on carbon basis, (ethylene leaving the reactor)/(ethylene+ethane leaving the reactor). It means the ethylene purity is the percentage of ethylene, on a carbon basis, present in the $C_2$ cut, containing close-boiling compounds, recovered in the stream leaving the reactor. The $C_2$ cut doesn't comprise the unconverted ethanol and acetaldehyde if any.

Experimental:

The stainless-steel reactor tube has an internal diameter of 11 mm. 10 ml of catalyst, as pellets of 35-45 mesh, is loaded in the tubular reactor. The void spaces before and after the catalyst bed are filled with inert alumina beads of 1.6 mm. The temperature profile is monitored with the aid of a thermowell placed inside the reactor. The reactor temperature is increased at a rate of 60° C./h to 550° C. under nitrogen, kept 1 hour at 550° C. and then cooled down to the initial reaction temperature under nitrogen. The nitrogen is then replaced by the feed at the indicated operating conditions.

Analysis of the products is performed by using an on-line gas chromatography.

Surfin 96 bio-ethanol

The characteristics of the Surfin 96 bio-ethanol used in the examples below are gathered table 1.

TABLE 1

Main characteristics of Surfin96 bio-ethanol

| | | Surfin 96 |
|---|---|---|
| Tot S | ppm | <0.2 |
| Tot N | ppm | <0.5 |
| Basic volatile | | |
| N | ppm | <1 |
| Na | mg/l | 0.5 |
| Ca | mg/l | <0.1 |
| Mn | mg/l | <0.1 |
| Fe | mg/l | <0.5 |
| Cu | mg/l | <0.2 |
| Zn | mg/l | <0.1 |
| Alcohol content | % vol @ 20° C. | 96.1 |
| Total acidity | g/hl acetic acid | 0.8 |
| Esters | g/hl | <0.1 |
| Acetaldehyde/Acetal | g/hl | <0.1 |

Catalyst:

The catalyst is a phosphorous modified zeolite (P-ZSM5), prepared according to the following recipe. A sample of zeolite ZSM-5 (Si/Al=13) in H-form was steamed at 550° C. for 6 h in 100% $H_2O$. The steamed solid was subjected to a contact with an aqueous solution of $H_3PO_4$ (85%$_w$t) for 2 h under reflux condition (4 ml/1 g zeolite). Then 69.9 g of CaCO3 was introduced. Then the solution was dried by evaporation for 3 days at 80° C. 750 g of the dried sample was extruded with 401.5 g of Bindzil and 0.01 wt % of extrusion additives. The extruded solid was dried at 110° C. for 16 h and calcinated at 600° C. for 10 h. The catalyst was then equilibrated 2 hours at 600° C. under steam.

Comparative Example 1

In this example, a mixture of 95% wt Surfin96 bio-ethanol and 5% wt water have been processed on the catalyst under the following dehydration conditions: outlet pressure of 2 bara, a weight hour space velocity referred to Surfin96 bio-ethanol of 7 $h^{-1}$, downflow, inlet temperature of 400° C. FIG. 1 shows the evolution of the ethanol conversion and the ethylene yield as a function of time on stream and shows that under the defined operating conditions, no catalyst deactivation occurs when processing pure ethanol as it is the case for Surfin 96 bio-ethanol.

TABLE 2

Performances of the dehydration catalyst at 400° C. under 2bara pressure using Surfin 96 bio-ethanol diluted with 5% wt water, the WHSV (ethanol) = 7 $h^{-1}$, 400° C.

| FEED | EtOH/H2O (95/5)% wt Surfin 96 |
|---|---|
| P (bara) | 2 |
| T (° C.) | 400 |
| WHSV (H−1) | 7 |
| EtOH conversion (% wt CH2) | 99.95 |
| DEE | 0.0 |
| Acetaldyde | 0.38 |
| Yield on C-basis (% wt CH2) | |
| CH4 | 0.0 |
| C2 | 0.21 |
| C2 = | 95.6 |
| C3 = | 0.9 |
| C4+ olef | 2.3 |
| C4+ paraf | 0.3 |
| Aromatics | 0.1 |
| Unknown | 0.13 |
| Selectivity on C-basis (% wt CH2) | |
| CH4 | 0.0 |
| C2 | 0.21 |
| C2 = | 95.7 |
| C3 = | 0.9 |
| C4+ olef | 2.3 |
| C4+ paraf | 0.3 |
| Aromatics | 0.1 |
| Unknown | 0.1 |
| C2's purity (%) | 99.79 |

Example 1

According to the Invention

Figure 2:
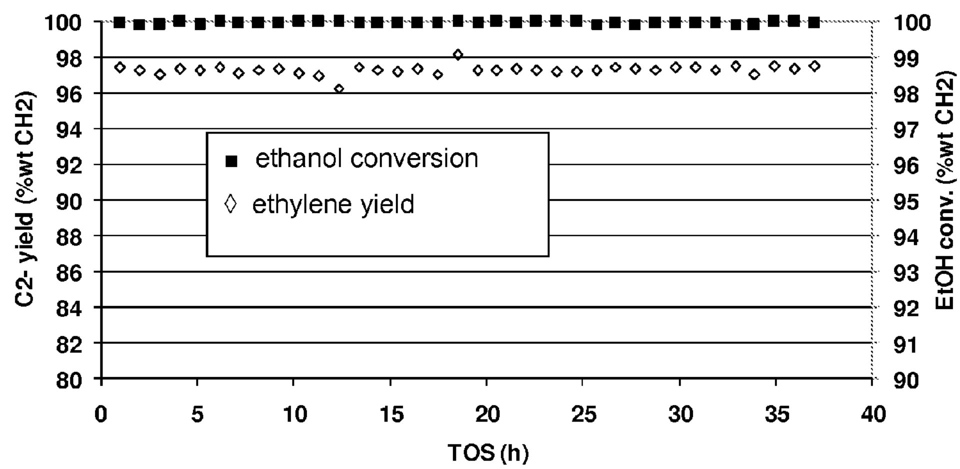
FIG. 2 shows the evolution of ethanol conversion and ethylene yield as a function of time on stream.

In this example, the bio-ethanol (Surfin 96) has been spiked with 0.8 wppm acetonitrile. A mixture of 95% wt of the spiked ethanol and 5% wt water have been processed on the catalyst under the following dehydration conditions: outlet pressure of 2 bara, a weight hour space velocity referred to raw ethanol of 7 $h^{-1}$, downflow. FIG. 2 shows the evolution of the ethanol conversion and the ethylene yield as a function of time on stream. The use of a controlled amount of neutralizing agent (in this case acetonitrile) allows to moderate the activity of the catalyst, therefore requiring a temperature increase (430° C. in this case), while improving the ethylene selectivity and without jeopardizing the time on stream performance as reported in table 3.

TABLE 3

Performances of the dehydration catalyst at 430° C. under 2bara pressure using bio-ethanol spiked with 0.8 ppm wt acetonitrile diluted with 5% wt water, the WHSV (ethanol) = 7 $h^{-1}$.

| FEED | EtOH/H2O (95/5)% wt Spiked bio-ethanol |
|---|---|
| P (bara) | 2 |
| T (° C.) | 430 |
| WHSV (H−1) | 7 |
| EtOH conversion (% wt CH2) | 99.97 |
| DEE | 0.0 |
| Acetaldyde | 0.27 |
| Yield on C-basis (% wt CH2) | |
| CH4 | 0.0 |
| C2 | 0.17 |
| C2 = | 97.3 |
| C3 = | 0.3 |
| C4+ olef | 1.1 |
| C4+ paraf | 0.1 |
| Aromatics | 0.7 |
| Unknown | 0.00 |
| Selectivity on C-basis (% wt CH2) | |
| CH4 | 0.0 |
| C2 | 0.17 |
| C2 = | 97.4 |
| C3 = | 0.3 |
| C4+ olef | 1.1 |
| C4+ paraf | 0.1 |
| Aromatics | 0.7 |
| Unknown | 0.0 |
| C2's purity (%) | 99.83 |

Example 2

Comparative Example

In this example, the bio-ethanol used is the Surfin96 bio-ethanol.

Figure 3:
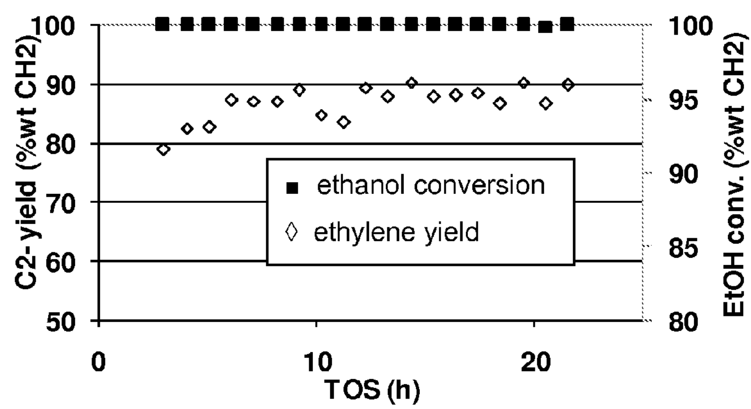
FIG. 3 shows the evolution of ethanol conversion and ethylene yield as a function of time on stream.

A mixture of 95% wt Surfin96 bio-ethanol and 5% wt water have been processed on the catalyst under the following dehydration conditions: outlet pressure of 2 bara, a weight hour space velocity referred to Surfin96 bio-ethanol of 7 h−1, downflow, 430° C. FIG. 3 shows the evolution of the ethanol conversion (filled symbols) and the ethylene yield (open symbols) as a function of time on stream. Table 4 gathers the performances of the dehydration catalyst. The results show that when processing Surfin 96 bio-ethanol at 430° C., secondary reactions (oligomerization/cracking) occur and impact significantly the final ethylene selectivity.

TABLE 4

Performances of the dehydration catalyst at 430° C. under 2bara outlet pressure using Surfin 96 bio-ethanol diluted with 5% wt water, the WHSV (ethanol) = 7 h−1.

| FEED | EtOH/H2O (95/5)% wt |
|---|---|
| P (bara) | 2 |
| T (° C.) | 430 |
| WHSV (H−1) | 7 |
| EtOH conversion (% wt CH2) | 99.99 |
| DEE | 0.0 |
| Acetaldyde | 0.11 |
| Yield on C-basis (% wt CH2) | |
| CH4 | 0.0 |
| C2 | 0.36 |
| C2 = | 86.8 |
| C3 = | 3.6 |
| C4+ olef | 7.5 |
| C4+ paraf | 0.9 |
| Aromatics | 0.3 |
| Unknown | 0.25 |

TABLE 4-continued

Performances of the dehydration catalyst at 430° C. under 2bara outlet pressure using Surfin 96 bio-ethanol diluted with 5% wt water, the WHSV (ethanol) = 7 h−1.

| FEED | EtOH/H2O (95/5)% wt |
|---|---|
| Selectivity on C-basis (% wt CH2) | |
| CH4 | 0.0 |
| C2 | 0.36 |
| C2 = | 86.8 |
| C3 = | 3.6 |
| C4+ olef | 7.5 |
| C4+ paraf | 0.9 |
| Aromatics | 0.3 |
| Unknown | 0.3 |
| C2's purity (%) | 99.58 |

What is claimed is:

1. A process comprising:

a) introducing in a reactor a stream (A) comprising ethanol, optionally water, and optionally an inert component, b) contacting said stream (A) with an acidic catalyst in said reactor at conditions effective to dehydrate at least a portion of the alcohol to make a corresponding olefin having the same number of carbon atoms as the alcohol, c) recovering from said reactor a stream (B) comprising the olefin, water and optionally the inert component and unconverted alcohol, d) optionally fractionating the stream (B) to recover the optional unconverted alcohol and recycling said optional unconverted alcohol to the reactor of step a), e) optionally fractionating the stream (B) to recover the optional inert component, the water and the olefin, and optionally recycling said optional inert component and optionally a part of the water to the reactor of step a), wherein:

f) introducing a component comprising a nitrile in stream (A) or directly in the reactor wherein the nitrile is in the amount ranging from 0.01 wppm to 10 wppm relative to the ethanol and is capable to neutralize a part of the catalyst active site; and g) optionally the temperature of the reactor is adjusted to increase the alcohol conversion, the olefin yield, or both.

2. A process comprising:

a) introducing in a reactor a stream (A) comprising ethanol, optionally water, optionally an inert component b) contacting said stream (A) with an acidic catalyst in said reactor at conditions effective to dehydrate at least a portion of the alcohol to make a corresponding olefin having the same number of carbon atoms as the alcohol, c) recovering from said reactor a stream (B) comprising the olefin, water and optionally the inert component and unconverted alcohol, d) optionally fractionating the stream (B) to recover the optional unconverted alcohol and recycling said optional unconverted alcohol to the reactor of step a), e) optionally fractionating the stream (B) to recover the optional inert component, the water and the olefin, and optionally recycling said optional inert component and optionally a part of the water to the reactor of step a), wherein:

f) introducing a component comprising nitrile in stream (A) or directly in the reactor wherein the component comprising nitrile is in the amount ranging from 0.01 wppm to 10 wppm relative to the ethanol and is capable to neutralize a part of the catalyst active site; and g) optionally the temperature of the reactor is adjusted to increase the alcohol conversion, the olefin yield, or both.

3. The process according to claim 1 or 2 wherein the catalyst is selected among:

a crystalline silicate zeolite having a ratio Si/A1 higher than 10, a dealuminated crystalline silicate zeolite, a phosphorous modified zeolite, silica-alumina, alumina, silicated, titanated, zirconated or fluorinated alumina or silico-aluminophosphates.

4. The process according to claim 1 or 2 wherein a part of the component introduced at step f) is already contained in the stream (A).

5. The process according to claim 1 or 2 wherein all the component introduced at step f) is already contained in the stream (A).

6. The process according to claim 1 or 2 wherein the component injected at step f) additionally comprises at least one from the group consisting of ammonia, organic ammonium salts, hydrazine, amines, amides, imines, di-imines, imides, cyanates, isocyanates, nitrites and nitroso compounds.

7. The process according to claim 1 or 2 wherein the component injected at step f) additionally comprises at least one from the group consisting of aldehydes, ketones and carboxylic esters.

8. The process according to claim 1 or 2 wherein the component injected at step f) additionally comprises at least one from the group consisting of thiols, sulphides and disulfides.

9. The process according to claim 1, wherein the component injected at step f) additionally comprises at least one from the group consisting of pyridines, pyrrols, pyrrolydones and pyrrolidines.

10. The process of claim 1, wherein the component injected at step f) additionally comprises at least one from the group consisting ammonia, organic ammonium salts, hydrazine, amides, imines, di-imines, imides, cyanates, isocyanates, nitrites, nitroso compounds, carboxylic esters, and thiols, disulfides.

11. The process of claim 1, wherein the component injected at step f) additionally comprises at least one from the group consisting ammonia, organic ammonium salts, hydrazine, amides, imines, di-imines, imides, cyanates, isocyanates, nitrites, and nitroso compounds.

12. The process of claim 1, wherein the stream (B) is fractionated to recover the unconverted alcohol, and the unconverted alcohol is recycled to the reactor of step a).

13. The process of claim 1, wherein the stream (B) is fractionated to recover the water and the olefin, and wherein a part of the water is recycled to the reactor of step a).

14. The process of claim 1, wherein the ethanol is a single alcohol introduced to the reactor.

15. The process of claim 1, wherein the temperature of the reactor is adjusted to increase the alcohol conversion, the olefin yield, or both.

16. The process of claim 15, wherein the temperature of the reactor is adjusted by increasing the temperature by an amount ranging from 5 to 50° C.

17. The process according to claim 1, wherein the catalyst is a dealuminated crystalline silicate zeolite.

18. The process according to claim 1, wherein the catalyst is a phosphorous modified zeolite made by a process comprising:

selecting a zeolite among the $H^+$ and $NH_4^+$ form of MFI, MEL, FER, MOR, clinoptilolite, MWW, TON, EUO, MFS and ZSM-48, wherein the selected zeolite has a Si/A1 ratio of 100 or lower;

steaming the selected zeolite at a temperature ranging from 400 to 870° C. for from 0.01-200 h;

leaching the steamed zeolite with an aqueous acid solution at conditions effective to remove a substantial part of Al from the steamed zeolite;

introducing phosphorous with an aqueous solution containing the source of phosphorous at conditions effective to introduce advantageously at least 0.05 wt % of the phosphorous;

separation of solid from liquid;

an optional washing step, an optional drying step, or an optional drying step followed by a washing step; and a calcination step.

19. A process comprising:

a) introducing in a reactor a stream (A) comprising ethanol, optionally water, optionally an inert component, b) contacting said stream (A) with an acidic catalyst in said reactor at conditions effective to dehydrate at least a portion of the alcohol to make a corresponding olefin having the same number of carbon atoms as the alcohol, c) recovering from said reactor a stream (B) comprising the olefin, water and optionally the inert component and unconverted alcohol, d) optionally fractionating the stream (B) to recover the optional unconverted alcohol and recycling said optional unconverted alcohol to the reactor of step a), e) optionally fractionating the stream (B) to recover the optional inert component, the water and the olefin, and optionally recycling said optional inert component and optionally a part of the water to the reactor of step a), wherein:

f) introducing a component comprising nitrile in stream (A) or directly in the reactor wherein the component comprising nitrile is in the amount ranging from 0.01 wppm to 10 wppm relative to the ethanol and is capable to neutralize a part of the catalyst active site; and g) optionally the temperature of the reactor is adjusted to increase the alcohol conversion, the olefin yield, or both;

and wherein the component introduced at step f) further comprises at least one from the group consisting of hydrazine, amines, amides, imines, di-imines, imides, cyanates, isocyanates, nitrites and nitroso compounds;

or selected from the group consisting of aldehydes, ketones and carboxylic esters;

or selected from the group consisting of thiols, sulphides and disulfides.

20. The process according to claim 19, wherein the component introduced at step f) is introduced by blending the component with the stream (A).

21. The process according to claim 19, wherein the component introduced at step f) is introduced by blending the component with a part of the stream (A) which is subsequently introduced in the reactor with a remaining part of the stream (A).

22. The process according to claim 19, wherein the component introduced at step f) is introduced by blending the component with the inert component which is subsequently introduced in the reactor with the stream (A).

23. The process according to claim 19, wherein the component introduced at step f) is introduced by blending the component with the water which is subsequently introduced in the reactor with the stream (A).

24. The process according to claim 19, wherein the component introduced at step f) is introduced by blending the component with a stream that is recycled back to the reactor comprising the unconverted alcohol, the water or the inert component.

25. The process according to claim 19, wherein the component introduced at step f) is introduced by blending an alcohol feedstock that is substantially free of the component with an alcohol feedstock containing the component.

* * * * *